United States Patent [19]
Heppke et al.

[11] Patent Number: 5,236,618
[45] Date of Patent: Aug. 17, 1993

[54] LIQUID CRYSTAL PHASE

[75] Inventors: Gerd Heppke; Feodor Oestreicher, both of Berlin, Fed. Rep. of Germany

[73] Assignee: Merck Patent Gesellschaft mit Beschrankter Haftung, Darmstadt, Fed. Rep. of Germany

[21] Appl. No.: 154,701

[22] Filed: Feb. 11, 1988

Related U.S. Application Data

[62] Division of Ser. No. 754,053, Jul. 11, 1985, Pat. No. 4,744,918.

[30] Foreign Application Priority Data

Jul. 11, 1984 [DE] Fed. Rep. of Germany ....... 3425503

[51] Int. Cl.$^5$ .................... C07K 19/34; C07K 19/30; C07K 19/12; G02F 1/13
[52] U.S. Cl. ...................... 252/299.61; 252/299.66; 252/299.63; 252/299.5; 252/299.68; 252/299.67
[58] Field of Search ........... 252/299.5, 299.67, 299.66, 252/299.63, 299.68, 299.61; 359/103

[56] References Cited

U.S. PATENT DOCUMENTS

| | | | |
|---|---|---|---|
| 4,243,740 | 1/1981 | Tsuda et al. | 252/299.01 |
| 4,556,727 | 12/1985 | Walba | 252/299.01 |
| 4,576,732 | 3/1986 | Isogai et al. | 252/299.01 |
| 4,615,586 | 10/1986 | Geary | 252/299.01 |
| 4,650,600 | 3/1787 | Heppke et al. | 252/299.61 |
| 4,713,197 | 12/1987 | Eidenschink et al. | 252/299.61 |
| 4,725,688 | 2/1988 | Taguchi et al. | 252/299.61 |
| 4,744,918 | 5/1988 | Heppke et al. | 252/299.61 |
| 4,752,414 | 6/1988 | Eidenschink et al. | 252/299.61 |
| 4,753,752 | 6/1988 | Raynes et al. | 252/299.01 |
| 4,775,223 | 10/1988 | Yoshinaga et al. | 252/299.01 |
| 4,784,793 | 11/1988 | Coates et al. | 252/299.01 |
| 4,812,259 | 3/1989 | Yoshinaga et al. | 252/299.01 |
| 4,820,839 | 4/1989 | Krause et al. | 252/299.61 |
| 4,824,217 | 4/1989 | Chan et al. | 252/299.01 |

FOREIGN PATENT DOCUMENTS

| | | | |
|---|---|---|---|
| 217240 | 4/1987 | European Pat. Off. | 252/299.01 |
| 3333677 | 4/1985 | Fed. Rep. of Germany | 252/299.63 |
| 1308237 | 2/1973 | United Kingdom | 252/299.68 |
| 2166754 | 5/1986 | United Kingdom | 252/299 |
| 2170214 | 7/1986 | United Kingdom | 252/299.01 |
| 8704705 | 8/1987 | World Int. Prop. O. | 252/299.01 |

OTHER PUBLICATIONS

Taniguchi, H., et al, Jap. J. Appl. Phys., vol. 26, No. 9, pp. L1558-L1560 (1987).

Taniguchi, H., et al., Ferroelectrics, vol. 77, pp. 137-144 (1988).
Taniguchi, et al., Jap. J. Appl. Phys., vol. 27, No. 4., pp. 452-455 (1988).

*Primary Examiner*—Robert L. Stoll
*Assistant Examiner*—C. Harris
*Attorney, Agent, or Firm*—Millen, White, Zelano & Branigan

[57] ABSTRACT

Liquid crystal phases containing at least one optically active compound of the formula I

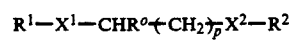

wherein
 X$^1$ and X$^2$ independently of one another are each —CO—O— or —O—CO—, one of X$^1$ and X$^2$ may also be —O—,
 R$^1$ and R$^2$ independently of one another are each a group —(A$^1$—Z)$_m$—(A$^2$)$_n$—Y, wherein
 A$^1$ and A$^2$ in each case independently of one another are a 1,4-phenylene, pyrimidine-2,5-diyl, pyrazine-2,5-diyl, pyridine-2,5-diyl, 1,4-cyclohexylene, 1,3-dioxane-2,5-diyl, 1,3-dithiane-2,5-diyl or 1,4-bicyclo(2,2,2)-octylene group, it also being possible for this to be monosubstituted or polysubstituted by F, Cl, Br, CN and/or alkyl groups with up to 12 C atoms, and it being possible for 1 or 2 non-adjacent CH$_2$ groups in the alkyl groups to be replaced by 0 atoms, Z is —CO—O—, —O—CO—, —CH$_2$CH$_2$—, —OCH$_2$—, —CH$_2$O—, —CH=N—, —N=CH—, —N=N—, —N(O)=N— or a single bond, m and n in each case independently of one another are 0, 1 or 2, Y is independently of one another a straight-chain or branched alkyl group with up to 12 C atoms, it being possible for 1 or 2 non-adjacent CH$_2$ groups to be replaced by 0 atoms, or, if n is 1 or 2, also F, Cl, Br or CN, R$^0$ is an alkyl group with up to 5 C atoms or a phenyl group or a cyclohexyl group, display largely temperature-independent electrooptical parameters.

16 Claims, No Drawings

LIQUID CRYSTAL PHASE

This is a division of application Ser. No. 754,053 filed Jul. 11, 1985, U.S. Pat. No. 4,744,918.

BACKGROUND OF THE INVENTION

Liquid crystal phases which form a helix structure with a given sense of rotation are increasingly required for liquid crystal displays. Thus, such materials are required, for example, for the Schadt-Helfrich effect in order to avoid the undesirable effect of "reverse twist" (E. Guyon and W. Urbach in "Nonemissive Electrooptic Displays", published by A. R. Kmetz, F. K. von Willisen, Plenum Press, New York-London, 1976, page 127), for the cholesteric-nematic phase transition effect and for bistability effects.

An important problem here is the production of a suitable temperature function of the pitch of the helix, which depends on the particular electrooptical effect and its specific design.

For liquid crystal display elements based on the twisted nematic cell, for example, a temperature-independent pitch is possible to avoid "reverse twist". It has furthermore been possible to show that compensation of the temperature drift of the threshold voltage of a twisted nematic cell can be achieved if the pitch of the helix decreases as the temperature increases (P. R. Gerber, Physics Letters 78A, 285 (1980)). The same applies to the phase transition effect, in that compensation of the threshold voltage drift is achieved by a helix pitch which decreases greatly as the temperature increases (A. Göbl-Wunsch, G. Heppke and F. Oestreicher, Journal de Physique 40, 773 (1979)).

The liquid crystal phases used for these purposes in general consist of mixtures of non-chiral liquid crystal compounds, to which chiral compounds are added to produce the helix structure. Virtually all the known chiral doping substances induce helix structures, the pitches of which increase over wide ranges to a greater or lesser degree as the temperature increases. Only certain spiro-biindane derivatives with a negative gradient of the temperature function are reported in the literature (Advances of Infrared and Raman Spectroscopy 8 (1981) Chapter 4). In practice, however, it was not possible to eliminate the troublesome temperature drift with these compounds. It has hitherto been possible to achieve the negative gradient in the temperature function frequently desired only by using two suitable doping substances with a different sense of rotation and a different relative temperature dependency (German Patent A-2,827,471). The disadvantages of this multiple doping process are, inter alia, the observance of the exact concentration ratio of the two chiral compounds, the restriction to a limited temperature range and the high total concentration necessary for the doping substances (A. Göbl-Wunsch, G. Heppke and G. Oestreicher, Journal de Physique, 40, 773 (1979)). External applications are therefore not possible.

SUMMARY OF THE INVENTION

It is therefore an object of this invention to provide a liquid crystal phase which has temperature-independent electrooptical parameters, in particular a temperature-independent threshold voltage, and achieves these properties using only a single doping substance.

It is another object of this invention to provide chiral compounds which induce a negative gradient in the temperature function of the pitch in liquid crystal phases for internal and external applications over a wide temperature range, coupled with a high twisting capacity.

Upon further study of the specification and appended claims, further objects and advantages of this invention will become apparent to those skilled in the art.

These objects have been achieved by providing the compounds of the formula I and the corresponding liquid crystal phase containing at least one of the compounds of formula I.

It has been found that the compounds of the formula I excellently meet the above requirements.

The invention thus relates to a liquid crystal phase containing at least one optically active compound of the formula I and to the new compounds which are of the formula

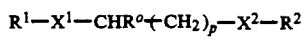

$$R^1-X^1-CHR^0-(CH_2)_p-X^2-R^2 \qquad I$$

wherein
  $X^1$ and $X^2$ independently of one another are each —CO—O— or —O—CO—, one of $X^1$ and $X^2$ may also be —O—,
  $R^1$ and $R^2$ independently of one another are each a group —$(A^1-Z)_m-(A^2)_n-Y$,
wherein
  $A^1$ and $A^2$ in each case independently of one another are a 1,4-phenylene, pyrimidine-2,5-diyl, pyrazine-2,5-diyl, pyridine-2,5-diyl, 1,4-cyclohexylene, 1,3-dioxane-2,5-diyl, 1,3-dithiane-2,5-diyl or 1,4-bicyclo(2,2,2)-octylene group, it also being possible for this to be monosubstituted or polysubstituted by F, Cl, Br, CN and/or alkyl groups with up to 12 C atoms, and it being possible for 1 or 2 non-adjacent $CH_2$ groups in the alkyl groups to be replaced by 0 atoms, Z is —CO—O—, —O—CO—, —$CH_2CH_2$—, —$OCH_2$—, —$CH_2O$—, —CH=N—, —N=CH—, —N=N—, —N(O)=N— or a single bond,
  m and n in each case independently of one another are 0, 1 or 2,
  Y is independently of one another a straight-chain or branched alkyl group with up to 12 C atoms, it being possible for 1 or 2 non-adjacent $CH_2$ groups to be replaced by 0 atoms, or, if n is 1 or 2, also F, Cl, Br or CN, with the proviso that (m+n) in at least one of the groups $R^1$ and $R^2$ is 2, 3 or 4, p is 0 or 1, and
  $R^0$ is an alkyl group with up to 5 C atoms or a phenyl group or a cyclohexyl group.

The invention furthermore relates to a liquid crystal display element containing a liquid crystal phase according to the invention.

The invention moreover relates to the use of compounds of the formula I for temperature compensation in liquid crystal phases.

The invention also relates to a method of temperature compensation in liquid crystal display elements containing a liquid crystal phase, at least 0.05% of at least one chiral compound of the formula I being admixed to the liquid crystal phase.

DETAILED DISCUSSION

Temperature-compensated liquid crystal phases or liquid crystal display elements are to be understood as meaning liquid crystal phases or liquid crystal display elements with largely temperature-independent electrooptical parameters, in particular with a largely temperature-independent threshold voltage. These temperature independencies generally extend over the range of normal uses, e.g., −40° C. to +100° C., preferably −20° C. to +80° C.

Herein, as is conventional, electro-optical properties are considered essentially independent of temperature if they vary by about ±0,4 percent or less per degree centigrade in the temperature range of 0° C. to 40° C., ±0,15 percent or less per degree centigrade or preferably ±0,05 percent or less per degree centigrade in the temperature range of −20° C. to +80° C. These deviations refer to the electro-optical properties at 20° C. Those of skill in the art will readily recognize that the nature of the temperature constancy will vary in accordance with the conventional stringency of the requirements for the particular application of interest.

The compounds of the formula I include novel optically active compounds of part formulae I', I'', Ib', Ib'', Ic' and Ic''.

$$Y-X^1-CHR^o-(CH_2)_p-X^2-(A^1-Z)_m-(A^2)_n-Y \quad I'$$
$$Y-(A^2)_n-(Z-A^1)_m-X^1-CHR^o-(CH_2)_p-X^2-Y \quad I''$$
$$Y-X^1-CHR^o-(CH_2)_p-X^2-A^1-A^2-Y \quad Ib'$$
$$Y-A^2-A^1-X^1-CHR^o-(CH_2)_p-X^2-Y \quad Ib''$$
$$Y-X^1-CHR^o-(CH_2)_p-X^2-A^1-Z-A^2-Y \quad Ic'$$
$$Y-A^2-Z-A^1-X^1-CHR^o-(CH_2)_p-X^2-Y \quad Ic''$$

In the compounds of the formulae I, I' and I'' those are preferred, wherein $A^1$ and $A^2$ are 1,4-phenylene or one of the groups $A^1$ and $A^2$ is 1,4-phenylene and the other group is pyrimidine-2,5-diyl, pyrazine-2,5-diyl or pyridine-2,5-diyl.

In the compounds of the formulae Ib' and Ib'' those are preferred wherein —$A^1$—$A^2$— is

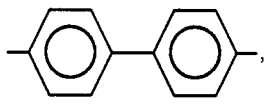

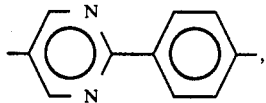

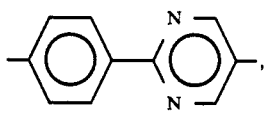

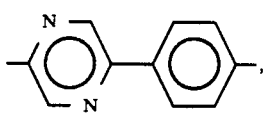

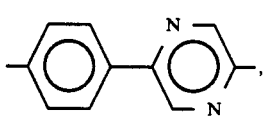

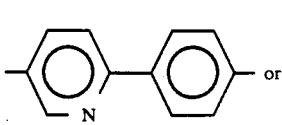 or

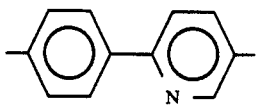

The novel, optically active compounds of the formula I are furthermore of importance as chiral doping materials for liquid crystal mixtures.

The compounds of the formula I include compounds of part formulae Ia to Im:

$$Y-CO-O-CHR^a-CH_2-O-CO-A^1-Y \quad Ia$$

$$Y-CO-O-CHR^a-CH_2-O-CO-A^1-A^2-Y \quad Ib$$

$$Y-CO-O-CHR^a-CH_2-O-CO-A^1-Z-A^2-Y \quad Ic$$

$$Y-CO-O-CHR^a-CH_2-O-CO-(A^1)_2-Z-A^2-Y \quad Id$$

$$Y-CC-O-CHR^a-CH_2-O-CO-A^1-Z-(A^1)_2-Y \quad Ie$$

$$Y-A^1-CO-O-CHR^a-CH_2-O-CO-A^1-Y \quad If$$

$$Y-A^1-CO-O-CHR^a-CH_2-O-CO-A^1-A^2-Y \quad Ig$$

$$Y-A^1-CO-O-CHR^a-CH_2-O-CO-A^1-Z-A^2-Y \quad Ih$$

$$Y-A^1-CO-O-CHR^a-CH_2-O-CO-(A^1)_2-Z-A^2-Y \quad Ii$$

$$Y-A^1-CO-O-CHR^a-CH_2-O-CO-A^1-Z-(A^2)_2-Y \quad Ij$$

$$Y-A^1-A^2-CO-O-CHR^a-CH_2-O-CO-A^1-A^2-Y \quad Ik$$

$$Y-A^1-A^2-CO-O-CHR^a-CH_2-O-CO-A^1-Z-A^2-Y \quad Il$$

$$Y-A^2-Z-A^1-CO-O-CHR^a-CH_2-O-CO-A^1-Z-A^2-Y \quad Im$$

In the compounds of the formulae above and below, Y is preferably alkyl, or furthermore alkoxy, another oxaalkyl group, CN or F.

In the compounds of the formulae above and below $R^0$ is preferably methyl or phenyl, p is preferably 1, $X^1$ is preferably —CO—O—, $X^2$ is preferably —O—CO— or —O—, Y is preferably straight-chain alkyl with up to 7 C-Atoms.

In the compounds of the formulae above and below, the alkyl radicals, in which also one ("alkoxy" or "oxaalkyl") or two $CH_2$ groups ("alkoxyalkoxy" or "dioxaalkyl") can be replaced by O atoms, can be straight-chain or branched. Preferably, they are straight-chain and have 2, 3, 4, 5, 6 or 7 C atoms, and are accordingly preferably ethyl, propyl, butyl, pentyl, hexyl, heptyl, ethoxy, propoxy, butoxy, pentoxy, hexoxy, heptoxy, 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl or 2-, 3-, 4-, 5- or 6-oxaheptyl or furthermore methyl, octyl, nonyl, decyl, methoxy, octoxy, nonoxy, decoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8-or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl or 1,3-, 1,4-, 1,5-, 1,6-, 2,4-, 2,5-, 2,6-, 3,5-, 3,6- or 4,6-dioxaheptyl.

Compounds of the formulae above with branched end group substituents Y can also be of importance. Branched groups of this type as a rule contain not more than one chain branching. Preferred branched radicals Y are isopropyl, 2-butyl (=1-methylpropyl), isobutyl (=2-methylpropyl), 2-methylbutyl, isopentyl (=3-methylbutyl), 2-methyl-pentyl, 3-methylpentyl, 2-ethylhexyl, 2-propylpentyl, isopropoxy, 2-methylpropoxy, 2-methylbutoxy, 3-methyl-butoxy, 2-methylpentoxy, 3-methylpentoxy, 2-ethylhexoxy, 1-methylhexoxy, 1-methylheptoxy, 2-oxa-3-methylbutyl or 3-oxa-4-methylpentyl.

Below, for simplicity, "Phe" is a 1,4-phenylene group, "Cy" is a 1,4-cyclohexylene group, "Dio" is a 1,3-dioxane-2,5-diyl group, "Bi" is a bicyclo-(2,2,2)-octylene group and "Pyr" is a pyrimidine-2,5-diyl group, a pyrazine-2,5-diyl group or a pyridine-2,5-diyl group, it being possible for these groups to be unsubstituted or monosubstituted or polysubstituted by F, Cl, Br, CN and/or alkyl groups with up to 12 C atoms, it being possible for 1 or 2 $CH_2$ groups in the alkyl groups to be replaced by 0 atoms.

$A^1$ and $A^2$ are in each case independently of one another preferably Cy, Phe or Dio; the compound of the formula I preferably contains not more than one of the radicals Dio, Bi or Pyr.

Z is preferably a single bond or a carboxyl group. Z is furthermore preferably a -$CH_2CH_2$- group. (m+n) is preferably 0, 1, 2 or 3, and particularly preferably 0 or 2.

Preferred groups $R_1$ and $R_2$ are:

—Cy—Phe—Y
—Phe—Cy—Y
—Phe—Phe—Y
—Cy—Cy—Y
—Phe—Phe—Phe—Y
—Cy—Phe—Phe—Y
—Cy—Cy—Phe—Y
—Dio—Phe—Phe—Y
—Dio—Cy—Y
—Dio—Phe—Y
—Pyr—Phe—Y
—Pyr—Cy—Y
—($A^1$)$_2$—$A^2$—Y
—$A^1$—$CH_2CH_2$—$A^2$—Y
—$A^1$—COO—$A^2$—Y
—$A^1$—OCO—$A^2$—Y
—Cy—Ph—$CH_2CH_2$—Cy—Y
—Cy—COO—Cy—Y
—Cy—COO—Ph—Y
—Ph—COO—Ph—Y $R^0$ is preferably a straight-chain alkyl group with up to 5 C atoms or a phenyl group, particularly preferably a methyl or a phenyl group. Suitable C 1-5 alkyl groups are those mentioned above.

Pyr is preferably a pyrimidine-2,5-diyl group.

The compounds of the formula I preferably contain 0, 1, 2, 3, 4, 5 or 6 ring structures $A^1$ and $A^2$. Compounds with 2 to 4 ring structures $A^1$ and $A^2$ are particularly preferred.

Of the compounds of the formulae I and Ia to Im, those in which at least one of the radicals contained therein has one of the preferred meanings mentioned are preferred.

The liquid crystal phases according to the invention comprise 2 to 18, preferably 3 to 15, components, at least one of which is a compound of the formula I. The other constituents are preferably chosen from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-bis-cyclohexylbiphenyls, phenyl- or cyclohexyl-pyrimidines, phenyl- or cyclohexyl-dioxanes, optionally halogenated stilbenes, benzyl phenyl ethers, tolanes and substituted cinnamic acids.

The most important compounds which are possible constituents of such liquid crystal phases can be characterised by the formula III $$R^3—L—G—E—R^4 \qquad III$$

wherein L and E are each a carbocyclic or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

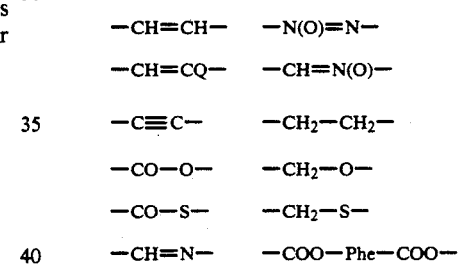

or a C—C single bond, Q is halogen, preferably chlorine, or —CN and $R^3$ and $R^4$ are each alkyl, alkoxy, alkanoyloxy or alkoxycarbonyloxy with up to 18, preferably up to 8, carbon atoms, or one of these radicals is also CN, NC, $NO_2$, $CF_3$, F, Cl or Br.

In most of these compounds, $R^3$ and $R^4$ are different, one of these radicals usually being an alkyl or alkoxy group. Other variants of the envisaged substituents are also customary. Many such substances or mixtures thereof are commercially available. All of these substances can be prepared by methods which are known from the literature.

The liquid crystal phases according to the invention contain at least 0.05% of at least one compound of the formula I. Preferably, they contain about 0.05 to 35%, in particular 0.1 to 10%, of one or more compounds of the formula I.

Liquid crystal phases according to the invention which are particularly preferred for liquid crystal dielectrics contain 0.1 to 3% of one or more compounds of the formula I. Dielectrics which contain only one compound of the formula I are particularly preferred.

The liquid crystal phases according to the invention are prepared in a manner which is known per se. As a rule, the components are dissolved in one another, advantageously at elevated temperature. By suitable additives, the liquid crystal phases according to the invention can be modified so that they can be used in all types of liquid crystal display elements which have hitherto been disclosed.

The compounds of the formula I can furthermore be used as liquid crystal phases for temperature indicators, also if appropriate without further components being admixed. When the compounds of the formula I are utilized alone as liquid phases, at least one of $R^1$ or $R^2$ contains two ring groups.

The abovementioned additives are known to the expert and are described in detail in the literature. It is possible to add, for example, conductive salts, preferably ethyl-dimethyl-dodecyl-ammonium 4-hexyloxybenzoate, tetrabutylammonium tetraphenylboranate or complex salts of crown ethers (compare, for example, I. Haller et al., Mol. Cryst. Liq. Cryst. Volume 24, pages 249-258 (1973)), to improve the conductivity, dichroic dyestuffs to produce colored guest/host systems or substances for modifying the dielectric anisotropy, viscosity and/or the orientation of the nematic phases. Such substances are described, for example, in German Offenlegungsschriften 2,209,127, 2,240,864, 2,321,632, 2,338,281, 2,450,088, 2,537,430, 2,853,728 and 2,902,177.

All of the chiral compounds required by this invention are known and/or readily prepared from known starting materials using fully conventional chemical methods and techniques. For those chiral compounds of this invention which are not per se known, they can be prepared by analogy to the known methods for preparing compounds which are already known. See for example Houben-Weyl, Methoden der Organischen Chemie (Methods of Organic Chemistry), Georg-Thieme Verlag, Stuttgart; Organic Reactions, John Wiley & Sons, Inc., N.Y.; Morrison and Mosher, Asymmetric Organic Reactions, Prentice-Hall, Inc., Englewood Cliffs, N.Y., 1971; Wilen, Top. Stereochem. 6, 107-176 (1971); March, Advanced Organic Chemistry, McGraw-Hill series in Advanced Chemistry, McGraw-Hill Kogakusha, Tokyo, 1977, whose disclosure is incorporated by reference herein. See also the examples herein which disclose typical conventional reactions which can be used to prepare the compounds useful in this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight, above and below.

In the examples, m.p. is the melting point. "Customary working up" means: water is added, the mixture is extracted with methylene chloride, the organic phase is separated off, dried and evaporated and the product is purified by crystallization and/or chromatography.

EXAMPLE 1

6.4 g of p-(trans-4-n-heptylcyclohexyl)-benzoyl chloride [obtainable by reacting p-(trans-4-n-heptylcyclohexyl)-benzoic acid with thionyl chloride] in 20 ml of toluene are added dropwise to a mixture of 0.8 g of (S)-1,2-propanediol, 20 ml of toluene and 2.4 ml of pyridine at 50°. The reaction mixture is boiled for 8 hours. The pyridinium chloride is filtered off hot with suction and the filtrate is worked up in the customary manner. Optically active 1,2-bis-(p-trans-4-n-heptylcyclohexylbenzoyloxy)-propane is obtained, m.p. 97°.

The following compounds are prepared analogously:
1,2-bis-(p-trans-4-ethylcyclohexylbenzoyloxy)-propane
1,2-bis-(p-trans-4-propylcyclohexylbenzoyloxy)-propane
1,2-bis-(p-trans-4-butylcyclohexylbenzoyloxy)-propane
1,2-bis-(p-trans-4-pentylcyclohexylbenzoyloxy)-propane
1,2-bis-(p-trans-4-hexylcyclohexylbenzoyloxy)-propane
1,2-bis-[p-(p'-trans-4-ethylcyclohexylphenyl)-benzoyloxy]-, propane
1,2-bis-[p-(p'-trans-4-propylcyclohexylphenyl)-benzoyloxy]-propane
1,2-bis-[p-(p'-trans-4-butylcyclohexylphenyl)-benzoyloxy]-propane
1,2-bis-[p-(p'-trans-4-pentylcyclohexylphenyl)-benzoyloxy]-propane
1,2-bis-[p-(p'-trans-4-hexylcyclohexylphenyl)-benzoyloxy]-propane
1,2-bis-[p-(p'-trans-4-heptylcyclohexylphenyl)-benzoyloxy]-propane
1,2-bis-[p-(p'-trans-4-octylcyclohexylphenyl)-benzoyloxy]-propane
1,2-bis-[p-(p'-trans-4-decylcyclohexylphenyl)-benzoyloxy]-propane
1,2-bis-(trans,trans-4-ethylcyclohexylcyclohexyl-4'-carbonyloxy)-propane
1,2-bis-(trans,trans-4-propylcyclohexylcyclohexyl-4'-carbonyloxy)-propane
1,2-bis-(trans,trans-4-butylcyclohexylcyclohexyl-4'-carbonyloxy)-propane
1,2-bis-(trans,trans-4-pentylcyclohexylcyclohexyl-4'-carbonyloxy)-propane
1,2-bis-(trans,trans-4-hexylcyclohexylcyclohexyl-4'-carbonyloxy)-propane
1,2-bis-(trans,trans-4-heptylcyclohexylcyclohexyl-4'-carbonyloxy)-propane
1,2-bis-(trans,trans-4-octylcyclohexylcyclohexyl-4'-carbonyloxy)-propane
1,2-bis-(trans,trans-4-decylcyclohexylcyclohexyl-4'-carbonyloxy)-propane
1,2-bis-[p-(p'-ethoxybenzoyloxy)-benzoyloxy]-propane
1,2-bis-[p-(p'-propoxybenzoyloxy)-benzoyloxy]-propane
1,2-bis-[p-(p'-butoxybenzoyloxy)-benzoyloxy]-propane
1,2-bis-[p-(p'-pentoxybenzoyloxy)-benzoyloxy]-propane
1,2-bis-[p-(p'-hexoxybenzoyloxy)-benzoyloxy]-propane, 133°
1,2-bis-[p-(p'-heptoxybenzoyloxy)-benzoyloxy]-propane
1,2-bis-[p-(p'-octoxybenzoyloxy)-benzoyloxy]-propane
1,2-bis-[p-(p'-decoxybenzoyloxy)-benzoyloxy]-propane
1,2-bis-[p-(p'-cyanobenzoyloxy)-benzoyloxy]-propane
1,2-bis-[p-(p'-ethylbenzoyloxy)-benzoyloxy]-propane
1,2-bis-[p-(p'-butylbenzoyloxy)-benzoyloxy]-propane
1,2-bis-[p-(p'-pentylbenzoyloxy)-benzoyloxy]-propane
1,2-bis-[p-(p'-heptylbenzoyloxy)-benzoyloxy]-propane
1,2-bis-(p-ethoxybenzoyloxy)-propane
1,2-bis-(p-propoxybenzoyloxy)-propane
1,2-bis-(p-butoxybenzoyloxy)-propane
1,2-bis-(p-pentoxybenzoyloxy)-propane
1,2-bis-(p-hexoxybenzoyloxy)-propane
1,2-bis-(p-heptoxybenzoyloxy)-propane
1,2-bis-(p-octoxybenzoyloxy)-propane
1,2-bis-(p-decoxybenzoyloxy)-propane
1,2-bis-(p-ethylbenzoyloxy)-propane 1,2-bis-(p-propylbenzoyloxy)-propane
1,2-bis-(p-butylbenzoyloxy)-propane
1,2-bis-(p-pentylbenzoyloxy)-propane
1,2-bis-(p-hexylbenzoyloxy)-propane
1,2-bis-(p-heptylbenzoyloxy)-propane
1,2-bis-(p-octylbenzoyloxy)-propane
1,2-bis-(p-decylbenzoyloxy)-propane
1,2-bis-(p-1-methylpropylbenzoyloxy)-propane
1,2-bis-(p-(R)-2-methylpropylbenzoyloxy)-propane
1,2-bis-(p-(R)-2-methylbutylbenzoyloxy)-propane
1,2-bis-(p-(S)-3-methylbutylbenzoyloxy)-propane
1,2-bis-(p-(R)-2-methylpentylbenzoyloxy)-propane
1,2-bis-(p-2-ethylhexylbenzoyloxy)-propane
1,2-bis-(p-(S)-2-methylpropoxybenzoyloxy)-propane
1,2-bis-(p-(R)-2-methylbutoxybenzoyloxy)-propane
1,2-bis-(p-(S)-3-methylbutoxybenzoyloxy)-propane
1,2-bis-(p-(R)-2-methylpentoxybenzoyloxy)-propane
1,2-bis-(p-2-ethylhexoxybenzoyloxy)-propane
1,2-bis-(p-(R)-2-oxa-3-methylbutylbenzoyloxy)-propane

EXAMPLE 2

6.4 g of p-(trans-4-n-heptylcyclohexyl)-benzoyl chloride in 20 ml of toluene are reacted with a mixture of 1.4 g of (R)-phenyl-1,2-ethanediol, 20 ml of toluene and 2.4 ml of pyridine in accordance with Example 1. Optically active 1,2-bis-(p-trans-4-n-heptyl-cyclohexylbenzoyloxy)-1-phenylethane is obtained, m.p. 124°.

The following compounds are prepared analogously:
1,2-bis-(p-trans-4-ethylcyclohexylbenzoyloxy)-1-phenylethane
1,2-bis-(p-trans-4-propylcyclohexylbenzoyloxy)-1-phenylethane
1,2-bis-(p-trans-4-butylcyclohexylbenzoyloxy)-1-phenylethane
1,2-bis-(p-trans-4-pentylcyclohexylbenzoyloxy)-1-phenylethane
1,2-bis-(p-trans-4-hexylcyclohexylbenzoyloxy)-1-phenylethane
1,2-bis-[p-(p'-trans-4-ethylcyclohexylphenyl)-benzoyloxy]-1-phenylethane
1,2-bis-[p-(p'-trans-4-propylcyclohexylphenyl)-benzoyloxy]-1-phenylethane
1,2-bis-[p-(p'-trans-4-butylcyclohexylphenyl)-benzoyloxy]-1-phenylethane
1,2-bis-[p-(p'-trans-4-pentylcyclohexylphenyl)-benzoyloxy]-1-phenylethane
1,2-bis-[p-(p'-trans-4-hexylcyclohexylphenyl)-benzoyloxy]-1-phenylethane
1,2-bis-[p-(p'-trans-4-heptylcyclohexylphenyl)-benzoyloxy]-1-phenylethane
1,2-bis-[p-(p'-trans-4-octylcyclohexylphenyl)-benzoyloxy]-1-phenylethane
1,2-bis-[p-(p'-trans-4-decylcyclohexylphenyl)-benzoyloxy]-1-phenylethane
1,2-bis-(trans,trans-4-ethylcyclohexylcyclohexyl-4'-carbonyloxy)-1-phenylethane
1,2-bis-(trans,trans-4-propylcyclohexylcyclohexyl-4'-carbonyloxy)-1-phenylethane
1,2-bis-(trans,trans-4-butylcyclohexylcyclohexyl-4'-carbonyloxy)-1-phenylethane
1,2-bis-(trans,trans-4-pentylcyclohexylcyclohexyl-4'-carbonyloxy)-1-phenylethane
1,2-bis-(trans,trans-4-hexylcyclohexylcyclohexyl-4'-carbonyloxy)-1-phenylethane
1,2-bis-(trans,trans-4-heptylcyclohexylcyclohexyl-4'-carbonyloxy)-1-phenylethane
1,2-bis-(trans,trans-4-octylcyclohexylcyclohexyl-4'-carbonyloxy)-1-phenylethane
1,2-bis-(trans,trans-4-decylcyclohexylcyclohexyl-4'-carbonyloxy)-1-phenylethane
1,2-bis-[p-(p'-ethoxybenzoyloxy)-benzoyloxy]-1-phenylethane
1,2-bis-[p-(p'-propoxybenzoyloxy)-benzoyloxy]-1-phenylethane
1,2-bis-[p-(p'-butoxybenzoyloxy)-benzoyloxy]-1-phenylethane
1,2-bis-[p-(p'-pentoxybenzoyloxy)-benzoyloxy]-1-phenylethane
1,2-bis-[p-(p'-hexoxybenzoyloxy)-benzoyloxy]-1-phenylethane, m.p. 133°
1,2-bis-[p-(p'-heptoxybenzoyloxy)-benzoyloxy]-1-phenylethane
1,2-bis-[p-(p'-octoxybenzoyloxy)-benzoyloxy]-1-phenylethane
1,2-bis-[p-(p'-decoxybenzoyloxy)-benzoyloxy]-1-phenylethane
1,2-bis-[p-(p'-cyanobenzoyloxy)-benzoyloxy]-1-phenylethane
1,2-bis-[p-(p'-ethylbenzoyloxy)-benzoyloxy]-1-phenylethane
1,2-bis-[p-(p'-butylbenzoyloxy)-benzoyloxy]-1-phenylethane
1,2-bis-[p-(p'-pentylbenzoyloxy)-benzoyloxy]-1-phenylethane
1,2-bis-[p-(p'-heptylbenzoyloxy)-benzoyloxy]-1-phenylethane
1,2-bis-(p-ethoxybenzoyloxy)-1-phenylethane
1,2-bis-(p-propoxybenzoyloxy)-1-phenylethane
1,2-bis-(p-butoxybenzoyloxy)-1-phenylethane
1,2-bis-(p-pentoxybenzoyloxy)-1-phenylethane
1,2-bis-(p-hexoxybenzoyloxy)-1-phenylethane
1,2-bis-(p-heptoxybenzoyloxy)-1-phenylethane
1,2-bis-(p-octoxybenzoyloxy)-1-phenylethane
1,2-bis-(p-decoxybenzoyloxy)-1-phenylethane
1,2-bis-(p-ethylbenzoyloxy)-1-phenylethane
1,2-bis-(p-propylbenzoyloxy)-1-phenylethane
1,2-bis-(p-butylbenzoyloxy)-1-phenylethane
1,2-bis-(p-pentylbenzoyloxy)-1-phenylethane
1,2-bis-(p-hexylbenzoyloxy)-1-phenylethane
1,2-bis-(p-heptylbenzoyloxy)-1-phenylethane
1,2-bis-(p-octylbenzoyloxy)-1-phenylethane
1,2-bis-(p-decylbenzoyloxy)-1-phenylethane
1,2-bis-(p-1-methylpropylbenzoyloxy)-1-phenylethane
1,2-bis-(p-(R)-2-methylpropylbenzoyloxy)-1-phenylethane
1,2-bis-(p-(R)-2-methylbutylbenzoyloxy)-1-phenylethane
1,2-bis-(p-(S)-3-methylbutylbenzoyloxy)-1-phenylethane
1,2-bis-(p-(R)-2-methylpentylbenzoyloxy)-1-phenylethane
1,2-bis-(p-2-ethylhexylbenzoyloxy)-1-phenylethane
1,2-bis-(p-(S)-2-methylpropoxybenzoyloxy)-1-phenylethane
1,2-bis-(p-(R)-2-methylbutoxybenzoyloxy)-1-phenylethane
1,2-bis-(p-(S)-3-methylbutoxybenzoyloxy)-1-phenylethane
1,2-bis-(p-(R)-2-methylpentoxybenzoyloxy)-1-phenylethane
1,2-bis-(p-ethylhexoxybenzoyloxy)-1-phenylethane
1,2-bis-(p-(R)-2-oxa-3-methylbutylbenzoyloxy)-1-phenylethane.

EXAMPLE 3

20 g of p-(trans-4-n-heptylcyclohexyl)-benzoyl chloride in 50 ml of toluene are reacted with a mixture of 5 g of (R)-cyclohexyl-1,2-ethanediol, 50 ml of toluene and 8 ml of pyridine in accordance with Example 1.

Optically active 1,2-bis-(p-trans-4-n-heptyl-cyclohexylbenzoyloxy)-1-cyclohexylethane is obtained.

The following compounds are prepared analogously:
1,2-bis-(p-trans-4-ethylcyclohexylbenzoyloxy)-1-cyclohexylethane
1,2-bis-(p-trans-4-propylcyclohexylbenzoyloxy)-1-cyclohexylethane
1,2-bis-(p-trans-4-butylcyclohexylbenzoyloxy)-1-cyclohexylethane
1,2-bis-(p-trans-4-pentylcyclohexylbenzoyloxy)-1-cyclohexylethane
1,2-bis-(p-trans-4-hexylcyclohexylbenzoyloxy)-1-cyclohexylethane
1,2-bis-[p-(p'-trans-4-ethylcyclohexylphenyl)-benzoyloxy]-1-cyclohexylethane
1,2-bis-[p-(p'-trans-4-propylcyclohexylphenyl)-benzoyloxy]-1-cyclohexylethane
1,2-bis-[p-(p'-trans-4-butylcyclohexylphenyl)-benzoyloxy]-1-cyclohexylethane
1,2-bis-[p-(p'-trans-4-pentylcyclohexylphenyl)-benzoyloxy]-1-cyclohexylethane
1,2-bis-[p-(p'-trans-4-hexylcyclohexylphenyl)-benzoyloxy]-1-cyclohexylethane
1,2-bis-[p-(p'-trans-4-heptylcyclohexylphenyl)-benzoyloxy]-1-cyclohexylethane
1,2-bis-[p-(p'-trans-4-octylcyclohexylphenyl)-benzoyloxy]-1-cyclohexylethane
1,2-bis-[p-(p'-trans-4-decylcyclohexylphenyl)-benzoyloxy]-1-cyclohexylethane
1,2-bis-(trans,trans-4-ethylcyclohexylcyclohexyl-4'-carbonyloxy)-1-cyclohexylethane
1,2-bis-(trans,trans-4-propylcyclohexylcyclohexyl-4'-carbonyloxy)-1-cyclohexylethane
1,2-bis-(trans,trans-4-butylcyclohexylcyclohexyl-4'-carbonyloxy)-1-cyclohexylethane
1,2-bis-(trans,trans-4-pentylcyclohexylcyclohexyl-4'-carbonyloxy)-1-cyclohexylethane
1,2-bis-(trans,trans-4-hexylcyclohexylcyclohexyl-4'-carbonyloxy)-1-cyclohexylethane
1,2-bis-(trans,trans-4-heptylcyclohexylcyclohexyl-4'-carbonyloxy)-1-cyclohexylethane
1,2-bis-(trans,trans-4-octylcyclohexylcyclohexyl-4'-carbonyloxy)-1-cyclohexylethane
1,2-bis-(trans,trans-4-decylcyclohexylcyclohexyl-4'-carbonyloxy)-1-cyclohexylethane
1,2-bis-[p-(p'-ethoxybenzoyloxy)-benzoyloxy]-1-cyclohexylethane
1,2-bis-[p-(p'-propoxybenzoyloxy)-benzoyloxy]-1-cyclohexylethane
1,2-bis-[p-(p'-butoxybenzoyloxy)-benzoyloxy]-1-cyclohexylethane
1,2-bis-[p-(p'-pentoxybenzoyloxy)-benzoyloxy]-1-cyclohexylethane
1,2-bis-[p-(p'-hexoxybenzoyloxy)-benzoyloxy]-1-cyclohexylethane,
1,2-bis-[p-(p'-heptoxybenzoyloxy)-benzoyloxy]-1-cyclohexylethane
1,2-bis-[p-(p'-octoxybenzoyloxy)-benzoyloxy]-1-cyclohexylethane
1,2-bis-[p-(p'-decoxybenzoyloxy)-benzoyloxy]-1-cyclohexylethane
1,2-bis-[p-(p'-cyanobenzoyloxy)-benzoyloxy]-1-cyclohexylethane
1,2-bis-[p-(p'-ethylbenzoyloxy)-benzoyloxy]-1-cyclohexylethane
1,2-bis-[p-(p'-butylbenzoyloxy)-benzoyloxy]-1-cyclohexylethane
1,2-bis-[p-(p'-pentylbenzoyloxy)-benzoyloxy]-1-cyclohexylethane
1,2-bis-[p-(p'-heptylbenzoyloxy)-benzoyloxy]-1-cyclohexylethane
1,2-bis-(p-ethoxybenzoyloxy)-1-cyclohexylethane
1,2-bis-(p-propoxybenzoyloxy)-1-cyclohexylethane
1,2-bis-(p-butoxybenzoyloxy)-1-cyclohexylethane
1,2-bis-(p-pentoxybenzoyloxy)-1-cyclohexylethane
1,2-bis-(p-hexoxybenzoyloxy)-1-cyclohexylethane
1,2-bis-(p-heptoxybenzoyloxy)-1-cyclohexylethane
1,2-bis-(p-octoxybenzoyloxy)-1-cyclohexylethane
1,2-bis-(p-decoxybenzoyloxy)-1-cyclohexylethane
1,2-bis-(p-ethylbenzoyloxy)-1-cyclohexylethane
1,2-bis-(p-propylbenzoyloxy)-1-cyclohexylethane
1,2-bis-(p-butylbenzoyloxy)-1-cyclohexylethane
1,2-bis-(p-pentylbenzoyloxy)-1-cyclohexylethane
1,2-bis-(p-hexylbenzoyloxy)-1-cyclohexylethane
1,2-bis-(p-heptylbenzoyloxy)-1-cyclohexylethane
1,2-bis-(p-octylbenzoyloxy)-1-cyclohexylethane
1,2-bis-(p-decylbenzoyloxy)-1-cyclohexylethane
1,2-bis-(p-1-methylpropylbenzoyloxy)-1-cyclohexylethane
1,2-bis-(p-(R)-2-methylpropylbenzoyloxy)-1-cyclohexylethane
1,2-bis-(p-(R)-2-methylbutylbenzoyloxy)-1-cyclohexylethane
1,2-bis-(p-(S)-3-methylbutylbenzoyloxy)-1-cyclohexylethane
1,2-bis-(p-(R)-2-methylpentylbenzoyloxy)-1-cyclohexylethane
1,2-bis-(p-2-ethylhexylbenzoyloxy)-1-cyclohexylethane
1,2-bis-(p-(S)-2-methylpropoxybenzoyloxy)-1-cyclohexylethane
1,2-bis-(p-(R)-2-methylbutoxybenzoyloxy)-1-cyclohexylethane
1,2-bis-(p-(S)-3-methylbutoxybenzoyloxy)-1-cyclohexylethane
1,2-bis-(p-(R)-2-methylpentoxybenzoyloxy)-1-cyclohexylethane
1,2-bis-(p-ethylhexoxybenzoyloxy)-1-cyclohexylethane
1,2-bis-(p-(R)-2-oxa-3-methylbutylbenzoyloxy)-1-cyclohexylethane.

EXAMPLE 4

0.8 g of 1-methoxy-2-propanol, 3.2 g of p-(p-n-octylphenyl)-benzoic acid chloride 20 ml of toluene and 2.1 ml of pyridine are boiled under reflux for 6 hours. The pyridinium chloride is filtered off hot with suction and the filtrate is worked up in the customary manner. Optically active 1-methoxy-2-[p-(p-n-octylphenyl)-benzoyloxy]-propane is obtained The following optically active compounds are prepared analogously:
1-methoxy-2-[p-(p-n-propylphenyl)-benzoyloxy]-propane
1-methoxy-2-[p-(p-n-pentylphenyl)-benzoyloxy]-propane
1-methoxy-2-[p-(p-n-hexylphenyl)-benzoyloxy]-propane
1-methoxy-2-[p-(p-n-heptylphenyl)-benzoyloxy]-propane 1-methoxy-2-[p-(p-n-hexylphenyl)-benzoyloxy]-propane
1-methoxy-2-[p-(p-n-decylphenyl)-benzoyloxy]-propane
1-methoxy-2-[p-(p-n-butoxyphenyl)-benzoyloxy]-propane
1-methoxy-2-[p-(p-n-hexoxyphenyl)-benzoyloxy]-propane
1-methoxy-2-[p-(p-n-heptoxyphenyl)-benzoyloxy]-propane
1-methoxy-2-[p-(p-n-octyloxyphenyl)-benzoyloxy]-propane
1-methoxy-2-[p-(p-n-nonoxyphenyl)-benzoyloxy]-propane
1-ethoxy-2-[p-(p-propylphenyl)-benzoyloxy]-propane
1-ethoxy-2-[p-(p-pentylphenyl)-benzoyloxy]-propane
1-ethoxy-2-[p-(p-hexylphenyl)-benzoyloxy]-propane
1-ethoxy-2-[p-(p-heptylphenyl)-benzoyloxy]-propane
1-ethoxy-2-[p-(p-octylphenyl)-benzoyloxy]-propane
1-ethoxy-2-[p-(p-nonylphenyl)-benzoyloxy]-propane
1-ethoxy-2-[p-(p-decylphenyl)-benzoyloxy]-propane
1-ethoxy-2-[p-(p-butoxyphenyl)-benzoyloxy]-propane
1-ethoxy-2-[p-(p-pentoxyphenyl)-benzoyloxy]-propane
1-ethoxy-2-[p-(p-hexoxyphenyl)-benzoyloxy]-propane
1-ethoxy-2-[p-(p-heptoxyphenyl)-benzoyloxy]-propane
1-ethoxy-2-[p-(p-octoxyphenyl)-benzoyloxy]-propane
1-ethoxy-2-[p-(p-nonoxyphenyl)-benzoyloxy]-propane
1-ethoxy-2-[p-(p-octanoyloxyphenyl)-benzoyloxy]-propane
1-propoxy-2-[p-(p-propylphenyl)-benzoyloxy]-propane
1-propoxy-2-[p-(p-butylphenyl)-benzoyloxy]-propane
1-propoxy-2-[p-(p-pentylphenyl)-benzoyloxy]-propane
1-propoxy-2-[p-(p-octylphenyl)-benzoyloxy]-propane
1-propoxy-2-[p-(p-nonylphenyl)-benzoyloxy]-propane
1-propoxy-2-[p-(p-decylphenyl)-benzoyloxy]-propane
1-propoxy-2-[p-(p-butoxyphenyl)-benzoyloxy]-propane
1-propoxy-2-[p-(p-pentoxyphenyl)-benzoyloxy]-propane
1-propoxy-2-[p-(p-hexoxyphenyl)-benzoyloxy]-propane
1-propoxy-2-[p-(p-heptoxyphenyl)-benzoyloxy]-propane
1-propoxy-2-[p-(p-octoxyphenyl)-benzoyloxy]-propane
1-propoxy-2-[p-(p-nonoxyphenyl)-benzoyloxy]-propane
1-propoxy-2-[p-(p-octanoyloxyphenyl)-benzoyloxy]-propane
1-propoxy-2-[p-(p-heptylphenyl)-benzoyloxy]-propane
1-butoxy-2-[n-(p-propylphenyl)-benzoyloxy-propane
1-butoxy-2-[p-(p-pentylphenyl)-benzoyloxy]-propane
1-butoxy-2-[p-(p-butylphenyl)-benzoyloxy]-propane
1-butoxy-2-[p-(p-heptylphenyl)-benzoyloxy]-propane
1-butoxy-2-[p-(p-octylphenyl)-benzoyloxy]-propane
1-butoxy-2-[p-(p-nonylphenyl)-benzoyloxy]-propane
1-butoxy-2-[p-(p-decylphenyl)-benzoyloxy]-propane
1-butoxy-2-[p-(p-butoxyphenyl)-benzoyloxy]-propane
1-butoxy-2-[p-(p-pentoxyphenyl)-benzoyloxy]-propane
1-butoxy-2-[p-(p-hexoxyphenyl)-benzoyloxy]-propane
1-butoxy-2-[p-(p-heptoxyphenyl)-benzoyloxy]-propane
1-butoxy-2-[p-(p-octoxyphenyl)-benzoyloxy]-propane
1-butoxy-2-[p-(p-nonoxyphenyl)-benzoyloxy]-propane
1-butoxy-2-[p-(p-octanoyloxyphenyl)-benzoyloxy]-propane

EXAMPLE 5

A solution of 11,6 g of dicyclohexylcarbodiimide in 6 ml of dichloromethane is added slowly to a solution of 15,2 g of 4-(5-n-nonylpyrimidinyl-2)-phenol, 5,2 g optically active 2-methyl-3-propoxy propionic acid and 0,62 g of 4-N,N-dimethyl-aminopyridine in 100 ml of dichloromethane at 0°, warmed up to room temperature and stirred for 2 hours. The urea derivative is filtered off, the filtrate is washed with dilute HCl and water and the organic phase is worked up as customary. Optically active 4-(5-n-nonylpyrimidinyl-2)-phenyl-2-methyl-3-propoxypropionate is obtained.

The following optically active compounds are prepares analogously:

4-(5-octylpyrimidinyl-2)-phenyl 2-methyl-3-propoxypropionate
4-(5-heptylpyrimidinyl-2)-phenyl 2-methyl-3-propoxypropionate
4-(5-hexylpyrimidinyl-2)-phenyl 2-methyl-3-propoxypropionate
4-(5-pentylpyrimidinyl-2)-phenyl 2-methyl-3-propoxypropionate
4-(5-butylpyrimidinyl-2)-phenyl 2-methyl-3-propoxypropionate
4-(5-propylpyrimidinyl-2)-phenyl 2-methyl-3-propoxypropionate
4-(5-nonylpyrimidinyl-2)-phenyl 2-methyl-3-methoxypropionate
4-(5-octylpyrimidinyl-2)-phenyl 2-methyl-3-methoxypropionate
4-(5-heptylpyrimidinyl-2)-phenyl 2-methyl-3-methoxypropionate
4-(5-hexylpyrimidinyl-2)-phenyl 2-methyl-3-methoxypropionate
4-(5-pentylpyrimidinyl-2)-phenyl 2-methyl-3-methoxypropionate
4-(5-butylpyrimidinyl-2)-phenyl 2-methyl-3-methoxypropionate
4-(5-nonylpyrimidinyl-2)-phenyl 2-methyl-3-butoxypropionate
4-(5-octylpyrimidinyl-2)-phenyl 2-methyl-3-butoxypropionate
4-(5-heptylpyrimidinyl-2)-phenyl 2-methyl-3-butoxypropionate
4-(5-hexylpyrimidinyl-2)-phenyl 2-methyl-3-butoxypropionate
4-(5-pentylpyrimidinyl-2)-phenyl 2-methyl-3-butoxypropionate
4-(5-butylpyrimidinyl-2)-phenyl 2-methyl-3-butoxypropionate
4-(5-nonylpyrimidinyl-2)-phenyl 2-methyl-3-pentoxypropionate
4-(5-octylpyrimidinyl-2)-phenyl 2-methyl-3-pentoxypropionate
4-(5-heptylpyrimidinyl-2)-phenyl 2-methyl-3-pentoxypropionate
4-(5-hexylpyrimidinyl-2)-phenyl 2-methyl-3-pentoxypropionate
4-(5-pentylpyrimidinyl-2)-phenyl 2-methyl-3-pentoxypropionate
4-(5-butylpyrimidinyl-2)-phenyl 2-methyl-3-pentoxypropionate
4-(5-nonylpyrimidinyl-2)-phenyl 2-methyl-3-heptoxypropionate
4-(5-octylpyrimidinyl-2)-phenyl 2-methyl-3-heptoxypropionate
4-(5-heptylpyrimidinyl-2)-phenyl 2-methyl-3-heptoxypropionate
4-(5-hexylpyrimidinyl-2)-phenyl 2-methyl-3-heptoxypropionate
4-(5-pentylpyrimidinyl-2)-phenyl 2-methyl-3-heptoxypropionate 4-(5-butylpyrimidinyl-2)-phenyl 2-methyl-3-heptoxypropionate
4-(5-nonylpyrazinyl-2)-phenyl 2-methyl-3-propoxypropionate
4-(5-octylpyrazinyl-2)-phenyl 2-methyl-3-propoxypropionate
4-(5-heptylpyrazinyl-2)-phenyl 2-methyl-3-propoxypropionate
4-(5-hexylpyrazinyl-2)-phenyl 2-methyl-3-propoxypropionate
4-(5-pentylpyrazinyl-2)-phenyl 2-methyl-3-propoxypropionate
4-(5-butylpyrazinyl-2)-phenyl 2-methyl-3-propoxypropionate
4-(5-nonylpyridinyl-2)-phenyl 2-methyl-3-propoxypropionate
4-(5-octylpyridinyl-2)-phenyl 2-methyl-3-propoxypropionate
4-(5-heptylpyridinyl-2)-phenyl 2-methyl-3-propoxypropionate
4-(5-hexylpyridinyl-2)-phenyl 2-methyl-3-propoxypropionate
4-(5-pentylpyridinyl-2)-phenyl 2-methyl-3-propoxypropionate
4-(5-butylpyridinyl-2)-phenyl 2-methyl-3-propoxypropionate
4-(5-nonylpyrimidinyl-2)-phenyl 3-methyl-3-propoxypropionate
4-(5-octylpyrimidinyl-2)-phenyl 3-methyl-3-propoxypropionate
4-(5-heptylpyrimidinyl-2)-phenyl 3-methyl-3-propoxypropionate
4-(5-hexylpyrimidinyl-2)-phenyl 3-methyl-3-propoxypropionate
4-(5-pentylpyrimidinyl-2)-phenyl 3-methyl-3-propoxypropionate
4-(5-butylpyrimidinyl-2)-phenyl 3-methyl-3-propoxypropionate

EXAMPLE 6

0.75 g of optically active 1-butyryloxy-2-propanol [obtainable by esterification of (S)-1,2-propanediol], 1,7 g of p-(p-n-octylphenyl)-benzoic acid chloride, 20 ml of toluene and 2,1 ml of pyridine are boiled under reflux for 6 hours. The pyridinium chloride is filtered off hot with suction and the filtrate is worked up in the customary manner. Optically active 1-butyryloxy-2-[p-(p-n-octylphenyl)-benzoyloxy]-propane is obtained.

The following optically active compounds are prepared analogously:
1-butyryloxy-2-[p-(p-nonylphenyl)-benzoyloxy]-propane
1-butyryloxy-2-[p-(p-heptylphenyl)-benzoyloxy]-propane
1-butyryloxy-2-[p-(p-hexylphenyl)-benzoyloxy]-propane
1-butyryloxy-2-[p-(p-pentylphenyl)-benzoyloxy]-propane
1-butyryloxy-2-[p-(p-butylphenyl)-benzoyloxy]-propane
1-butyryloxy-2-[p-(p-propylphenyl)-benzoyloxy]-propane
1-butoxy-2-(p-(p-nonylphenyl)-benzoyloxy]-propane
1-butoxy-2-(p-(p-octylphenyl)-benzoyloxy]-propane
1-butoxy-2-(p-(p-heptylphenyl)-benzoyloxy]-propane
1-butoxy-2-(p-(p-hexylphenyl)-benzoyloxy]-propane
1-butoxy-2-(p-(p-pentylphenyl)-benzoyloxy]-propane
1-butoxy-2-(p-(p-butylphenyl)-benzoyloxy]-propane
1-butoxy-2-(p-(p-propylphenyl)-benzoyloxy]-propane
1-methoxy-2-(p-(p-nonylphenyl)-benzoyloxy]-propane
1-methoxy-2-(p-(p-octylphenyl)-benzoyloxy]-propane
1-methoxy-2-(p-(p-heptylphenyl)-benzoyloxy]-propane
1-methoxy-2-(p-(p-hexylphenyl)-benzoyloxy]-propane
1-methoxy-2-(p-(p-pentylphenyl)-benzoyloxy]-propane
1-methoxy-2-(p-(p-butylphenyl)-benzoyloxy]-propane
1-methoxy-2-(p-(p-propylphenyl)-benzoyloxy]-propane
1-heptoxy-2-(p-(p-nonylphenyl)-benzoyloxy]-propane
1-heptoxy-2-(p-(p-octylphenyl)-benzoyloxy]-propane
1-heptoxy-2-(p-(p-heptylphenyl)-benzoyloxy]-propane
1-heptoxy-2-(p-(p-hexylphenyl)-benzoyloxy]-propane
1-heptoxy-2-(p-(p-pentylphenyl)-benzoyloxy]-propane
1-heptoxy-2-(p-(p-butylphenyl)-benzoyloxy]-propane
1-heptoxy-2-(p-(p-propylphenyl)-benzoyloxy]-propane
1-butoxy-1-[p-(p-nonylphenyl)-benzoyloxy]-ethane
1-butoxy-1-[p-(p-octylphenyl)-benzoyloxy]-ethane
1-butoxy-1-[p-(p-heptylphenyl)-benzoyloxy]-ethane
1-butoxy-1-[p-(p-hexylphenyl)-benzoyloxy]-ethane
1-butoxy-1-[p-(p-pentylphenyl)-benzoyloxy]-ethane
1-butoxy-1-[p-(p-butylphenyl)-benzoyloxy]-ethane
1-butoxy-1-[p-(p-propylphenyl)-benzoyloxy]-ethane
1-butoxy-1-[p-(5-nonylpyrimidinyl-2)-benzoyloxy]-ethane
1-butoxy-1-[p-(5-octypyrimidinyl-2)-benzoyloxy]-ethane
1-butoxy-1-[p-(5-heptylpyrimidinyl-2)-benzoyloxy)-ethane
1-butoxy-1-[p-(5-hexylpyrimidinyl)-2-benzoyloxy)-ethane
1-butoxy-1-[p-(5-pentylpyrimidinyl-2)-benzoyloxy]-ethane
1-butoxy-1-[p-(5-butylpyrimidinyl-2)-benzoyloxy]-ethane
1-butoxy-1-[p-(5-propylpyrimidinyl-2)-benzoyloxy]-ethane The following are examples of liquid crystal phases according to the invention containing at least one optically active compound of the formula I. In each case the absolute value of the pc-product is given.

EXAMPLE A

A liquid crystal phase of 2.0% of 1,2-bis-(p-trans-4-n-heptylcyclohexylbenzoyloxy)-propane, dissolved in RQ-TN 404 [commercially available nematic liquid crystal mixture based on cyanopyrimidines] has a pc-product [p=pitch in μm; c=concentration in % by weight], with left-handedness of the helix structure, of 26.8 μm.% by weight at 12°.

EXAMPLE B

The liquid crystal phase from Example A exhibits a pc-product, with left-handedness of the helix structure, of 28.0 (33.7) μm.% by weight at 19° (28°).

EXAMPLE C

The liquid crystal phase from Example A exhibits a pc-product, with left-handedness of the helix structure, of 40.0 (47.4) μm.% by weight at 38° (48°).

EXAMPLE D

The liquid crystal phase from Example A exhibits a pc-product, with left-handedness of the helix structure, of 53.3 (175.6) μm.% by weight at 58° (79°).

EXAMPLE E

The liquid crystal phase from Example A exhibits a pc-product, with left-handedness of the helix structure, of 377.2 μm.% by weight at 84°.

EXAMPLE F

The liquid crystal phase from Example A exhibits a pc-product, with right-handedness of the helix structure, of 187.5 μm.% by weight at 102°.

EXAMPLE G

A liquid crystal phase of 0.2% of 1,2-bis-(p-trans-4-n-heptylcyclohexylbenzoyloxy)-1-phenylethane, dissolved in RO-TN 404, exhibits a pc-product, with left-handedness of the helix structure, of 3.7 μm.% by weight at 23°.

EXAMPLE H

The liquid crystal phase from Example G has a pc-product, with left-handedness of the helix structure, of in each case 3.7 μm.% by weight at 43° (83°).

EXAMPLE I

A liquid crystal phase of 2.4% of 1,2-bis-(p-trans-4-n-heptylcyclohexylbenzoyloxy)-1-phenylethane, dissolved in RO-TN 404, has a pc-product of 4.2 μm.% by weight at 28°.

EXAMPLE J

A liquid crystal phase of 8.0% of 1,2-bis-(p-trans-4-n-heptylcyclohexylbenzoyloxy)-1-phenylethane, dissolved in RO-TN 404, has an absorption band at 660 nm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a liquid crystal phase comprising at least two liquid crystalline compounds, the improvement wherein at least one compound in said phase is an optically active compound of the formula $R^1-X^1-CHR^0(CH_2)_pX^2-R^2$ wherein
  $X^2$ is —O— and $X^1$ is —O—CO—,
  each of $R^1$ and $R^2$ independently is —($A^1$—Z)$_m$—($A^2$)$_n$—Y,
  each of $A^1$ and $A^2$ independently is a 1,4-phenylene (Phe), pyrimidine-2,5-diyl (Pyr), 1,4-cyclohexylene (Cy), 1,3-dioxane-2,5-diyl (Dio), 1,3-dithiane-2,5-diyl, pyrazine-2,5-diyl, pyridine-2,5-diyl, or 1,4-bicyclo (2,2,2)-octylene (Bi) or one of said $A^1$ and $A^2$ groups monosubstituted or polysubstituted by F, Cl, Br, CN, alkyl of 1-12 C atoms, $C_{1-12}$-alkyl, wherein 1 or 2 non-adjacent $CH_2$ groups are replaced by O atoms, or a combination thereof;
  Z is —$CH_2CH_2$—, —$OCH_2$—, —$CH_2O$—, —CH=N—, —N=CH—, N=N, —N(O)=N—, or a single bond;
  each of m and n independently is 0, 1, or 2;
  each Y independently is alkyl of 1-12 C atoms or $C_{1-12}$-alkyl, wherein 1 or 2 non-adjacent $CH_2$ groups are replaced by O atoms or, when n is 1 or 2, Y can also be F, Cl, Br, or CN;
  p is 1; and
  $R^0$ is methyl with the proviso that (m+n) in $R^1$ is 2, 3, or 4.

2. A phase of claim 1, wherein said optically active compound is of the formula:

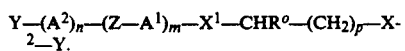

3. A phase of claim 1, wherein said optically active compound is of the formula

4. A phase of claim 1, wherein in said compound, $A^1$ and $A^2$ are 1,4-phenylene.

5. A phase of claim 1, wherein in said compound, one of $A^1$ and $A^2$ is a 1,4-phenylene group and the other is a pyrimidine-2,5-diyl, pyrazine-2,5-diyl or pyridine-2,5-diyl group.

6. A phase of claim 1, wherein in said compound, —$A^2$—$A^1$— is

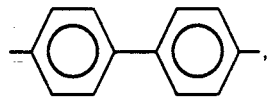

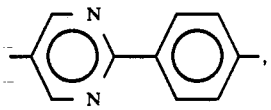

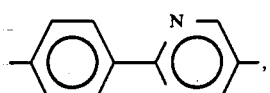

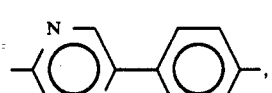

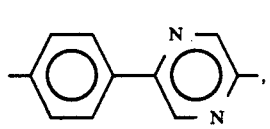

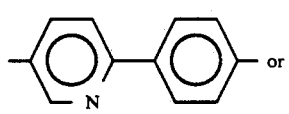 or

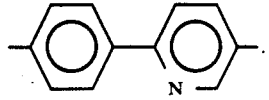

7. A phase of claim 1, wherein in said compound, Y is straight-chain alkyl of up to 7 C atoms.

8. A phase according to claim 1 wherein in said optically active compound, for each of $R^1$ and $R^2$, n+m=2 or 3.

9. A phase according to claim 1 wherein in said optically active compound, Y is alkyl or alkoxy.

10. A phase according to claim 1 wherein in said optically active compound, $A^1$ and $A^2$ are Cy, Phe, or Dio.

11. A phase according to claim 1 wherein in said optically active compound, $A^1$ and $A^2$ are Cy or Phe.

12. A phase according to claim 1 wherein in said optically active compound, not more than one Dio, Bi, or Pyr is contained.

13. A phase according to claim 1 comprising about 0.05 to 35% of at least one of said optically active compounds.

14. A phase according to claim 13 wherein said percentage is 0.1 to 3%.

15. In a liquid crystal display element comprising a liquid crystal phase, the improvement wherein said phase is one of claim 1.

16. In a liquid crystal display element comprising a liquid crystal phase, the improvement wherein said phase is one of claim 14.

* * * * *